United States Patent [19]

Hathaway

[11] 4,036,235
[45] July 19, 1977

[54] DRAINAGE DEVICE FOR EAR IRRIGATION

[76] Inventor: Lucille Hathaway, 4855 Monroe St., Lot 612, Toledo, Ohio 43623

[21] Appl. No.: 583,587

[22] Filed: June 4, 1975

[51] Int. Cl.² .................. A61F 11/00; A61F 13/00
[52] U.S. Cl. .................................. 128/292; 128/151; 128/248
[58] Field of Search ............... 128/275, 132 R, 132 D, 128/283, 295, 292, 286, 151, 248, 227, 241; 2/209

[56] References Cited

U.S. PATENT DOCUMENTS

| | | | |
|---|---|---|---|
| 636,462 | 11/1899 | Small | 128/292 |
| 1,143,046 | 6/1915 | Gilmore | 128/292 |
| 3,447,536 | 6/1969 | Snyder | 128/283 |
| 3,841,325 | 10/1974 | Pickard | 128/151 |

Primary Examiner—Robert W. Michell
Assistant Examiner—Henry S. Layton
Attorney, Agent, or Firm—Malcolm W. Fraser

[57] ABSTRACT

A drainage device for irrigation of the ear comprises a receptacle of clear flexible plastic which has an inner wall formed with an opening through which the outer ear projects, thereby aiding in positioning and supporting the same. A band or tie strings on the upper edge of the inner receptacle wall embraces the patient's head and supports the weight of the receptacle. From the bottom of the receptacle extends a drainage tube which can be conveniently clipped to the patient's garment. To enable the receptacle to fit in leak-proof manner, surgical appliance adhesive secures the receptacle around the front and lower part of the outer ear.

2 Claims, 3 Drawing Figures

DRAINAGE DEVICE FOR EAR IRRIGATION

SUMMARY OF THE INVENTION

Ear irrigation has always been a problem for the individual because of the added work of handling the drainage. To attend to irrigation and, at the same time handle the drainage, usually requires more than one person. According to this invention, ear irrigation and the necessary drainage can be conveniently attended to by the patient without assistance. This is due to a light weight, basin-like device through which the outer ear extends for ready access and which is supported from the head. A drainage tube leads from the device to a suitable discharge. The area in front of and below the ear are rendered leak-proof to militate against leakage on the patient.

DESCRIPTION OF PREFERRED EMBODIMENT

Figures 1, 2:
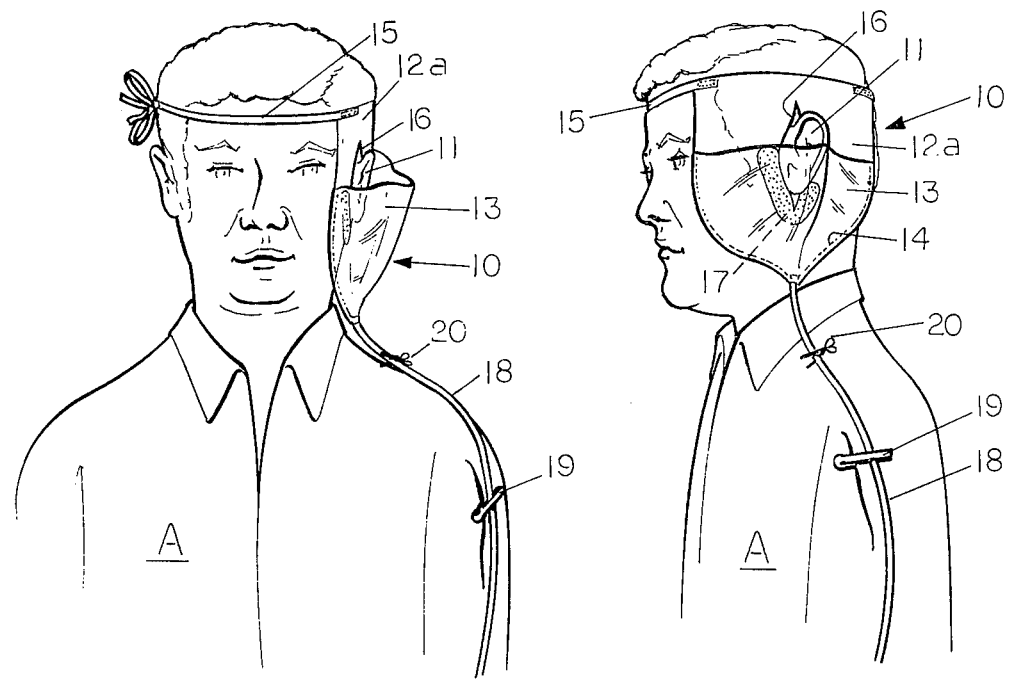
FIG. 1 is a front view of a patient equipped with a drainage device for ear irrigation, showing a front elevation of the latter.
FIG. 2 is a side view of the patient showing the drainage device in side elevation.
Figure 3:
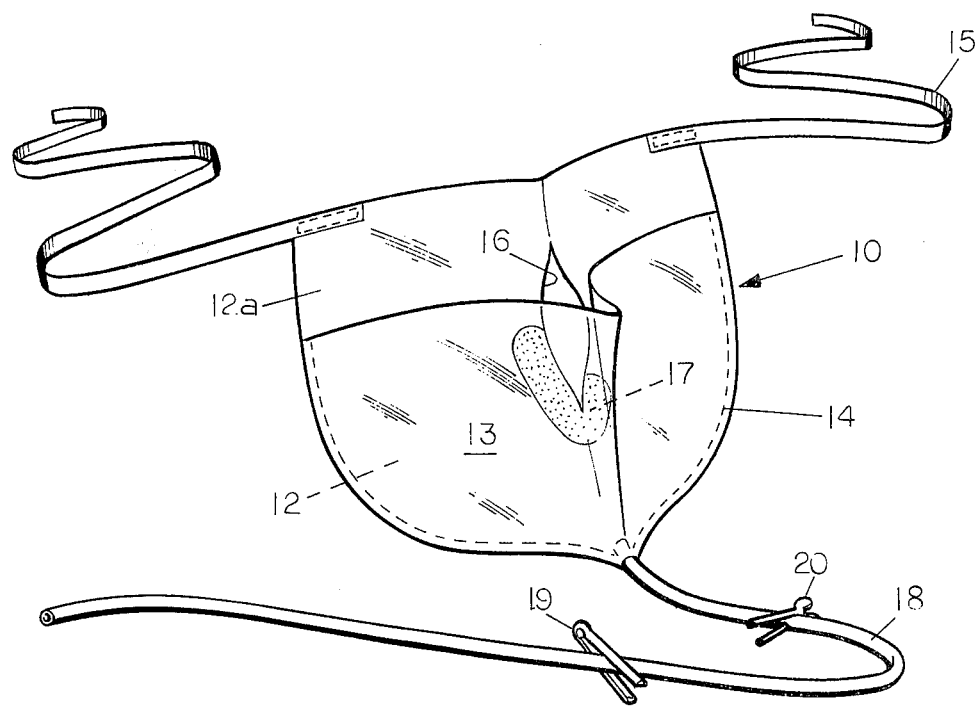
FIG. 3 is an enlarged side elevation of the drainage device.

The illustrated embodiment of the invention shows a patient A to whom is applied, on the outer ear, a drainage device 10 for ear irrigation. The device comprises a receptacle of clear, flexible, plastic material which may be regarded as disposable or reusable, and is formed with a flat inner wall 12 to which a somewhat wider flat outer wall 13 is secured by a sewed seam 14. The opposite walls 12 and 13 form a basin which can expand to approximately the level of the meatus to the auditory canal for enabling convenient entry to the ear.

The receptacle is supported on the patient's head so that he can, without assistance, perform ear irrigation. For this purpose, the inner wall 12 has an upwardly disposed integratl extension 12a which leads to a position about in line with the patient's forehead. At the edge portion of the extension 12a are attached tie strings 15 which can embrace the head and be tied in place. Alternatively, an elastic band (not shown) may replace the tie strings 15.

Formed centrally to the inner wall 12 and extending into the extention 12a is a vertically elongate narrow opening 16 of generally diamond shape which is properly proportioned to slip over the patient's ear 11 substantially as shown. Due to the flexibility and some resilience of the material, the ear is engaged with some degree of snugness in order to militate against the irrigating liquid leaking from the receptacle or basin. Since no two ears are alike, the opening 16 must be a general compromise in size. It will be noted that a substantial portion of the depth of the receptacle is below the opening 16 to insure proper reception of liquid.

To effect a leak-proof connection around the front and lower part of the outer ear 11, surgical appliance adhesive 17 may be used in appropriate places as indicated on the drawing.

Liquid in the receptacle or basin is drained through a tube 18 of desired length leading from the bottom of the receptacle. This tube is conveniently retained in position by a suitable clip 19 attached to the patient's clothing.

Clamp 20 on the tube 18 may be employed for retaining solid particles in the receptacle for examination when such test is required. Any suitable form of clamp may be used for this purpose.

Not only is the device above described admirably adapted for use in ear irrigation, but it can also be used in ear examination, curretement of impact cerumen, and also a foundation for a sterile field in special treatment of the ear. Where irrigation is not indicated, the receptable may serve as a receiver for dry waste.

Numerous changes in details of construction, arrangement and choice of materials may be made without departing from the spirit of the invention.

What I claim is:

1. Drainage device for ear irrigation comprising
   a. receptacle having a flat flexible inner wall and a somewhat eider outer flexible wall secured at its side edge portions to said inner wall expand outwardly to form a basin,
   b. an upward extension on said inner wall, providing a substantial head-engaging portion above the upper edge of said outer wall,
   c. strap attaching means on the upper part of said extension embracingly to engage the patient's forehead,
   d. a vertically elongate opening of generally diamond shape in said inner wall and extending into said extension and enabling the patient's ear to be slipped therethrough so that the upper edge of said basin is approximately level with the meatus of the auditory canal, and
   e. a discharge tube leading from the bottom of said basin.

2. Drainage device for ear irrigation as claimed in claim 1, comprising surgical appliance adhesive on said inner wall in the region of the lower part of said opening for providing a leak-proof connection between the device and the patient.

* * * * *